US008501766B2

(12) United States Patent
Kaye et al.

(10) Patent No.: US 8,501,766 B2
(45) Date of Patent: Aug. 6, 2013

(54) TREATMENT OF RHEUMATOID ARTHRITIS WITH A COMBINATION OF LAQUINIMOD AND METHOTREXATE

(75) Inventors: Joel Kaye, Netanya (IL); Eran Blaugrund, Rehovot (IL); Nora Tarcic, Modiin (IL)

(73) Assignee: Teva Pharmaceutical Industries Ltd., Petach Tikva (IL)

( * ) Notice: Subject to any disclaimer, the term of this patent is extended or adjusted under 35 U.S.C. 154(b) by 289 days.

(21) Appl. No.: 13/039,188

(22) Filed: Mar. 2, 2011

(65) Prior Publication Data

US 2011/0218203 A1 Sep. 8, 2011

Related U.S. Application Data

(60) Provisional application No. 61/339,375, filed on Mar. 3, 2010.

(51) Int. Cl.
- *A01N 43/42* (2006.01)
- *A01N 43/90* (2006.01)
- *A61K 31/44* (2006.01)
- *A61K 31/519* (2006.01)

(52) U.S. Cl.
USPC ..................................... 514/299; 514/262.1

(58) Field of Classification Search
USPC . 514/250, 262.1, 313; 544/350, 255; 546/134
See application file for complete search history.

(56) References Cited

U.S. PATENT DOCUMENTS

| | | | |
|---|---|---|---|
| 4,107,310 A | 8/1978 | Allais et al. |
| 4,547,511 A | 10/1985 | Eriksoo et al. |
| 4,738,971 A | 4/1988 | Eriksoo et al. |
| 5,716,638 A | 2/1998 | Touitou |
| 5,912,349 A | 6/1999 | Sih |
| 6,077,851 A | 6/2000 | Bjork et al. |
| 6,121,287 A | 9/2000 | Bjork et al. |
| 6,133,285 A | 10/2000 | Bjork et al. |
| 6,307,050 B1 | 10/2001 | Kwiatkowski et al. |
| 6,395,750 B1 | 5/2002 | Hedlund et al. |
| 6,593,343 B2 | 7/2003 | Bjork et al. |
| 6,605,616 B1 | 8/2003 | Bjork et al. |
| 6,696,407 B1 | 2/2004 | Longo et al. |
| 6,875,869 B2 | 4/2005 | Jansson |
| 7,485,311 B2 | 2/2009 | Lue et al. |
| 7,560,100 B2 | 7/2009 | Pinchasi et al. |
| 7,560,557 B2 | 7/2009 | Jansson |
| 7,589,208 B2 | 9/2009 | Jansson et al. |
| 7,884,208 B2 | 2/2011 | Frenkel et al. |
| 2002/0173520 A1 | 11/2002 | Bjork et al. |
| 2005/0074451 A1 | 4/2005 | Yednock et al. |
| 2006/0004019 A1 | 1/2006 | Lieberburg |
| 2007/0086979 A1 | 4/2007 | Chevrier et al. |
| 2007/0207141 A1 | 9/2007 | Lieberburg |
| 2007/0231319 A1 | 10/2007 | Yednock |
| 2007/0293537 A1 | 12/2007 | Patashnik et al. |
| 2008/0044382 A1 | 2/2008 | Lieberburg |
| 2008/0063607 A1 | 3/2008 | Tamarkin et al. |
| 2008/0090897 A1 | 4/2008 | Steiner et al. |
| 2008/0108641 A1 | 5/2008 | Ajami |
| 2008/0118553 A1 | 5/2008 | Frenkel et al. |
| 2008/0166348 A1 | 7/2008 | Kupper et al. |
| 2008/0206159 A1 | 8/2008 | Tamarkin et al. |
| 2009/0048181 A1 | 2/2009 | Schipper et al. |
| 2009/0062330 A1 | 3/2009 | Kalafer et al. |
| 2009/0081259 A1 | 3/2009 | Jonas et al. |
| 2009/0148462 A1 | 6/2009 | Chevrier et al. |
| 2009/0156542 A1 | 6/2009 | Purschke et al. |
| 2009/0162432 A1 | 6/2009 | Safadi et al. |
| 2009/0221575 A1 | 9/2009 | Gerber et al. |
| 2009/0232889 A1 | 9/2009 | Jansson et al. |
| 2010/0055072 A1 | 3/2010 | Gant et al. |
| 2010/0322900 A1 | 12/2010 | Tarcic et al. |
| 2011/0027219 A1 | 2/2011 | Tarcic et al. |
| 2011/0034508 A1 | 2/2011 | Hayardeny |
| 2011/0112141 A1 | 5/2011 | Frenkel et al. |
| 2011/0118308 A1 | 5/2011 | Frenkel et al. |
| 2011/0217295 A1 | 9/2011 | Haviv et al. |
| 2011/0218179 A1 | 9/2011 | Haviv et al. |
| 2011/0251235 A1 | 10/2011 | Patashnik et al. |
| 2012/0010238 A1 | 1/2012 | Piryatinsky et al. |
| 2012/0010239 A1 | 1/2012 | Fristedt |

(Continued)

FOREIGN PATENT DOCUMENTS

| | | |
|---|---|---|
| EP | 1073639 | 11/2002 |
| EP | 1097139 | 11/2002 |

(Continued)

OTHER PUBLICATIONS

PCT International Preliminary Report on Patentability issued Sep. 4, 2012 in connection with PCT International Application No. PCT/US2011/026789.

PCT International Preliminary Report on Patentability issued Sep. 4, 2012 in connection with PCT International Application No. PCT/US2011/026885.

PCT International Preliminary Report on Patentability issued Sep. 4, 2012 in connection with PCT International Application No. PCT/US2011/026891.

Office Action issued by the U.S. Patent and Trademark Office on Nov. 5, 2012 in connection with U.S. Appl. No. 13/039,194.

Office Action issued by the U.S. Patent and Trademark Office on Dec. 4, 2012 in connection with U.S. Appl. No. 13/039,178.

(Continued)

*Primary Examiner* — Kendra D Carter
(74) *Attorney, Agent, or Firm* — John P. White; Gary J. Gershik; Cooper & Dunham LLP

(57) ABSTRACT

This invention provides a method of treating a subject afflicted with rheumatoid arthritis comprising periodically administering to the subject an amount of laquinimod or pharmaceutically acceptable salt thereof and an amount of methotrexate, wherein the amounts when taken together are effective to treat the subject. This invention also provides laquinimod or pharmaceutically acceptable salt thereof for use in combination with methotrexate in treating a subject afflicted with rheumatoid arthritis. This invention also provides a pharmaceutical composition comprising an amount of laquinimod or pharmaceutically acceptable salt thereof and an amount of methotrexate for use in treating a subject afflicted with rheumatoid arthritis.

10 Claims, 3 Drawing Sheets

U.S. PATENT DOCUMENTS

| | | | |
|---|---|---|---|
| 2012/0142730 A1 | 6/2012 | Tarcic et al. | |
| 2012/0225124 A1 | 9/2012 | Safadi et al. | |
| 2012/0302600 A1 | 11/2012 | Patashnik et al. | |
| 2013/0028866 A1 | 1/2013 | Gilgun et al. | |
| 2013/0029916 A1 | 1/2013 | Gilgun et al. | |

FOREIGN PATENT DOCUMENTS

| | | |
|---|---|---|
| EP | 1095021 | 9/2003 |
| EP | 1720531 | 11/2006 |
| EP | 1511732 | 12/2006 |
| WO | WO 99/55678 | 11/1999 |
| WO | WO 00/03991 | 1/2000 |
| WO | WO 00/03992 | 1/2000 |
| WO | WO 03/106424 | 12/2003 |
| WO | WO 2005/074899 | 8/2005 |
| WO | WO 2007/139887 | 12/2007 |
| WO | WO 2008/079270 | 7/2008 |
| WO | WO 2008/085484 | 7/2008 |
| WO | WO 2010/057006 | 5/2010 |

OTHER PUBLICATIONS

Fauci et al. (2008) "Diagnostic Criteria for Systemic Lupus Erythematosus" in Harrison's Principles of Internal Medicine, (Eds.), McGraw Hill (New York), p. 2077.

Sztejnbok et al. (1971) "Azathioprine in the Treatment of Systemic Lupus Erythematosus" Arthr. Rheum. 14, 639-45.

Gordon et al. (2003) "Definition and treatment of lupus flares measured by the BILAG index" Rheumatol. 42, 1372-79.

Ponticelli (2006) "New Therapies for Lupus Nephritis" Clin J Am Soc Nephrol, vol. 1, pp. 863-868.

Morris et al, (1981) "Systemic Lupus Erythematosus with Nephritis" Archives of Disease in Childhood, Vol, 56, pp. 779-783.

Galinsky et al. "Basic Pharmacokinetics and Pharmacodynamics" in Remington: The Scinece and Practice of Pharmacy (Baltimore, Lippincott Williams & Wilkins, 2006), p. 1171.

Reagan-Shaw et al. (2007) "Dose translation from animal to human sturdies revisited" FASEB J 22:659-661.

"Guidance for Industry—Estimating the Maximum Safe Starting Dose in Initial Clinical Trials for Therapeutics in Adult Healthy Volunteers" Jul. 2005.

Written Opinion of the International Searching Authority issued Aug. 19, 2010 in connection with PCT International Application No. PCT/US2010/01759, filed Jun. 18, 2010.

PCT International Search Report issued Aug. 19, 2010 in connection with PCT International Application No. PCT/US2010/01759, filed Jun. 18, 2010.

Written Opinion of the International Searching Authority issued Oct. 5, 2010 in connection with PCT International Application No. PCT/US2010/02194, filed Aug. 9, 2010.

PCT International Search Report issued Oct. 5, 2010 in connection with PCT International Application No. PCT/US2010/02194, filed Aug. 9, 2010.

Written Opinion of the International Searching Authority issued Sep. 7, 2010 in connection with PCT International Application No. PCT/US2010/02129 filed Jul. 29, 2010.

PCT International Search Report issued Sep. 7, 2010 in connection with PCT International Application No. PCT/US2010/02129 filed Jul. 29, 2010.

Written Opinion of the International Searching Authority issued Apr. 12, 2011 in connection with PCT International Application No. PCT/US2011/26879, filed Mar. 2, 2011.

PCT International Search Report issued Apr. 12, 2011 in connection with PCT International Application No. PCT/US2011/26879, filed Mar. 2, 2011.

Written Opinion of the International Searching Authority issued Apr. 29, 2011 in connection with PCT International Application No. PCT/US11/26885, filed Mar. 2, 2011.

PCT International Search Report issued Apr. 29, 2011 in connection with PCT International Application No. PCT/US11/26885, filed Mar. 2, 2011.

Written Opinion of the International Searching Authority issued May 19, 2011 in connection with PCT International Application No. PCT/US11/26891, filed Mar. 2, 2011.

PCT International Search Report issued May 19, 2011 in connection with PCT International Application No. PCT/US11/26891, filed Mar. 2, 2011.

Acheson, et al. (1995) "A BDNF autocrine loop in adult sensory neurons prevents cell death", Nature, 374(6521):450-3.

Alonso, et al. (2005) "Endogenous BDNF is required for long-term memory formation in the rat parietal cortex", Learning & Memory, 12:504-510.

Amaral, et al. (2007) "TRPC channels as novel effectors of BDNF signaling: Potential implications for Rett syndrome", Pharmacol Ther, 113(2007):394-409.

Barkhof, F. (1999) "MRI in Multiple Sclerosis: Correlation with Expanded Disability Status Scale (EDSS)", Multiple Sclerosis, 5(4):283-286.

Boneschi, et al. (2003) "Effects of glatiramer acetate on relapse rate and accumulated disbility in multiple sclerosis . . . ", Multiple Sclerosis, 9(4):349-355.

Caffe, et al. (2001) "A combination of CNTF and BDNF rescues rd photoreceptors . . . ", Investigative Ophthalmology & Visual Science, 42:275-82.

Chesselet, MF. (2003) "Dopamine and Parkinson's disease: is the killer in the house?" Molecular Psychiatry, 8:369-370.

Ciammola, et al. (2007) "Low brain-derived neurotrophic factor (BDNF) levels in serum of Huntington's disease patients", Am J Med Gent Part B, 144b:574-577.

ClinicalTrials.gov. Bethesda (MD): Natl Lib Med. Aug. 18, 2008 ID NCT00737932, Laquinimod Ph IIa Study . . . http://clinicaltrials.gov/ct2/show/NCT00737932?term=Crohns&recr=Open&rank=2.

Comi, et al, (2007) LAQ/5062 Study Group. "The Effect of Two Doses of Laquinimod . . . " Presented at 59th Ann. Mtg of the American Aced. of Neurology; Apr. 28-May 5, 2007 Boston, MA.

De Stefano, et al. (1999) "Evidence of early axonal damage in patients with multiple sclerosis", Arch Neurol, 2001;58:65-70.

EMEA Guideline on Clinical Investigation of Medicinal Products for the Treatment of Multiple Sclerosis (CPMP/EWP/561/98 Rev. 1, Nove.2006).

Hohlfeld, et al. (2000) "The neuroprotective effect of inflammation: implications for the therapy of multiple sclerosis", J Neuroimmunol, 107(2000):161-166.

Howells, et al. (2000) "Reduced BDNF mRNA expression in the Parkinson's disease substantia nigra", Experimental Neurology, 166(1):127-135.

Huang, EJ and Reichardt, LF (2001) "Neurotrophins: roles in neuronal development and function", Annu. Rev. Neurosci, 24:677-736.

Hyman, et at, (1991) "BDNF is a neurotrophic factor for dopaminergic neurons of the substantia nigra", Nature, 350(6315):230-2.

Katoh-Semba, et al. (2002) "Riluzole enhances expression of brain-derived neurotrophic factor with consequent proliferation . . . ", FASEB J, 16:1328-30.

Maker, et al. (2008) "Brain derived neurotrophic factor treatment reduces inflammation and apoptosis in . . . ", Journal of the Neurological Sciences, 270(1-2):70-76.

Miki, et al. (1999) "Relapsing-Remitting Multiple Sclerosis: Longitudinal Analysis of MR Images . . . ", Radiology, 213:395-399.

Mix, et al. (2008) "Animal models of multiple sclerosis for the development and validation of novel therapies—potential and limitations", Journal of Neurology, 255(6):7-14.

Molteni, et al. (2006) "Abstract: Chronic treatment with fluoxetine [Prozac®] up-regulates cellular BDNF mRNA expression in rat . . . ", Int J Neuropsychopharmacol, 9(3):307-17.

Monteggia, L. (2007) "Elucidating the role of brain-derived neurotrophic factor in the brain", Am J Psychiatry, 164:1790.

Neuhaus, et al. (2003) "Immunomodulation in multiple sclerosis: from immunosuppression to neuroprotection", Trends Pharmacol Sci, 24:131-138.

Noseworthy, et al. (2000) "Multiple sclerosis", N Engl J Med, 343:938-952.

Polman, et al. (2005) "Diagnostic criteria for multiple sclerosis: 2005 revisions to the McDonald Criteria", Annals of Neurology, 58(6):840-846.

Polman, et al. (2005) "Treatment with laquinimod reduces development of active MRI lesions in relapsing MS", Neurology, 64:987-991.

Preiningerova, J. (2009) "Oral laquinimod therapy in relapsing multiple sclerosis", Expert Opinion on Investigational Drugs, 18(7):985-989.

Riviere, M. (1998) "An analysis of extended survival in patients with amyotrophic lateral sclerosis treated with riluzole", Arch Neurol, 55:526-8.

Rudick, R. (1999) "Disease-Modifying Drugs for Relapsing-Remitting Multiple Sclerosis and Future Directions for . . . Therapeutics", Neurotherapeutics, 56:1079-1084.

Sandberg-Wollheim, et al. (2005) "48-Week Open Safety Study with a High-Dose Oral . . . " Therapy-Immunomodulation—Part II, Sep. 30, 2005. 15:30-17:00 (abstract only).

Seri, et al. (2006) "Serum brain-derived neurotrophic factor, depression, and antidepressant medications: meta-analyses and implications", Biol Psychiatry, 64:527-532.

Snider, et al. (1989) "Neurotrophic molecules", Ann Neurol, 26(4):489-506.

Teva Press Release, "Laquinimod Demonstrated Significant and sustained Impact on Multiple Sclerosis Disease Activity", Sep. 18, 2008.

Tramontina, et al. (2009) "Brain-derived neurotrophic factor serum levels before and after treatment for acute mania", Neuroscience Letters, 452:111-3.

Tuvessen et al. (2005) "Cytochrome P450 3A4 is the major enzyme responsible for the metabolism of laquinimod, a novel immu . . . ", Drug Metabolism and Disposition. 33(6):866-872.

TREATMENT OF RHEUMATOID ARTHRITIS WITH A COMBINATION OF LAQUINIMOD AND METHOTREXATE

This application claims the benefit of U.S. Provisional Application No. 61/339,375, filed Mar. 3, 2010, the entire content of which is hereby incorporated by reference herein.

Throughout this application, various publications are referred to by first author and year of publication. Full citations for these publications are presented in a References section immediately before the claims. Disclosures of the publications cited in the References section in their entireties are hereby incorporated by reference into this application in order to more fully describe the state of the art as of the date of the invention described herein.

BACKGROUND

Rheumatoid Arthritis

Rheumatoid arthritis (RA) is a chronic syndrome characterized by non-specific, usually symmetric inflammation of the peripheral joints, potentially resulting in progressive destruction of articular and periarticular structures, with or without generalized manifestations. Although its precise etiology has not yet been determined, genetic predisposition has been determined. In addition, environmental factors are thought to play a role. (The Merck Manual, 7th Ed.)

According to the American College of Rheumatology (1987), at least four of the following criteria have to be met before a condition is classified as rheumatoid arthritis (Arnett, 1988): 1) morning stiffness of >1 hour most mornings for at least 6 weeks; 2) arthritis and soft-tissue swelling of >3 of 14 joints/joint groups, present for at least 6 weeks; 3) arthritis of hand joints, present for at least 6 weeks; 4) symmetric arthritis, present for at least 6 weeks; 5) subcutaneous nodules in specific places; 6) rheumatoid factor at a level above the 95th percentile; and 7) radiological changes suggestive of joint erosion.

There is no known cure for rheumatoid arthritis, but many different types of treatment are available to alleviate symptoms and/or modify the disease process. Pharmacological treatment of RA includes nonsteroidal anti-inflammatory drugs and salicylates (NSAIDs), slow-acting drugs, gold compounds, hydroxychloroquine, sulfasalazine, combinations of slow-acting drugs, corticosteroids, and cytotoxic or immunosuppressive drugs. Other forms of treatment include rest, nutrition, exercise, physiotherapy and surgery. (The Merck Manual, $7^{th}$ Ed.)

Laquinimod

Laquinimod is a novel synthetic compound with high oral bioavailability which has been suggested as an oral formulation for the treatment of Multiple Sclerosis (MS) (Polman, 2005; Sandberg-Wollheim, 2005). Laquinimod and its sodium salt form are described, for example, in U.S. Pat. No. 6,077,851. The effects of laquinimod in combination with methotrexate on rheumatoid arthritis have not been reported.

Methotrexate

Methotrexate (MTX) is an antimetabolite drug used in treatment of cancer and autoimmune diseases. It acts by inhibiting the metabolism of folic acid via the inhibition of dihydrogolate redutase and blocks DNA synthesis in rapidly proliferate cells. These actions induce immunosuppression.

MTX is sold under the brand names Rheumatrex® and Trexall™. Rheumatrex® and Trexall™ are indicated to treat certain kinds of cancer, psoriasis and rheumatoid arthritis.

Cytotoxic/immunosuppressive drugs including MTX are increasingly used for severe, active RA. These drugs can suppress inflammation and may allow reduction of corticosteroid doses. (The Merck Manual, $7^{th}$ Ed.)

The recommended dosage for severe rheumatoid arthritis in humans (consensus-based) is: initial 10 to 15 mg orally once weekly, increased by 5 mg/week every 2 to 3 weeks, up to a maximum of 20 to 30 mg/week. The manufacturer's recommended dosage for severe rheumatoid arthritis in humans is: initial 7.5 mg orally once weekly or 2.5 mg orally every 12 hours for 3 doses once weekly, up to a maximum of 20 mg/week. (Physicians' Desk Reference)

Combination Therapy

The administration of two drugs to treat a given condition, such as rheumatoid arthritis, raises a number of potential problems. In vivo interactions between two drugs are complex. The effects of any single drug are related to its absorption, distribution, and elimination. When two drugs are introduced into the body, each drug can affect the absorption, distribution, and elimination of the other and hence, alter the effects of the other. For instance, one drug may inhibit, activate or induce the production of enzymes involved in a metabolic route of elimination of the other drug (Guidance for Industry, 1999). Thus, when two drugs are administered to treat the same condition, it is unpredictable whether each will complement, have no effect on, or interfere with, the therapeutic activity of the other in a human subject.

Not only may the interaction between two drugs affect the intended therapeutic activity of each drug, but the interaction may increase the levels of toxic metabolites (Guidance for Industry, 1999). The interaction may also heighten or lessen the side effects of each drug. Hence, upon administration of two drugs to treat a disease, it is unpredictable what change will occur in the negative side profile of each drug.

Additionally, it is difficult to accurately predict when the effects of the interaction between the two drugs will become manifest. For example, metabolic interactions between drugs may become apparent upon the initial administration of the second drug, after the two have reached a steady-state concentration or upon discontinuation of one of the drugs (Guidance for Industry, 1999).

SUMMARY OF THE INVENTION

This invention provides a method of treating a subject afflicted with rheumatoid arthritis comprising periodically administering to the subject an amount of laquinimod or pharmaceutically acceptable salt thereof and an amount of methotrexate, wherein the amounts when taken together are effective to treat the subject.

This invention also provides laquinimod or pharmaceutically acceptable salt thereof for use in combination with methotrexate in treating a subject afflicted with rheumatoid arthritis.

This invention also provides a pharmaceutical composition comprising an amount of laquinimod or pharmaceutically acceptable salt thereof and an amount of methotrexate for use in treating a subject afflicted with rheumatoid arthritis.

BRIEF DESCRIPTION OF THE DRAWINGS

FIG. 1 is a graph of Individual Histopathologic Parameters (Six Joint): a bar graph showing the mean scores (of the six joints) for each histopathologic parameter in the Control and Treatment Groups. ("LAQ" indicates Laquinimod, "MTX" indicates methotrexate) (*p≦0.05 student's t-test to vehicle, #p≦0.05 student's t-test to vehicle, n=10/ treatment group, n=4/normal control.) The y-axis shows mean±SE individual histopathology parameters (six joints) (scored: 0—normal, 1=minimal, 2=mild, 3=moderate, 4=marked, and 5=severe)

The left most bar in each Treatment Group (black) represent inflammation. The bar second from the left in each Treatment Group (light grey) represents pannus. The bar third from the left in each Treatment Group (white) represents cartilage damage, and the bar fourth from the left in each Treatment Group (dark grey) represents bone damage.

Figure 2:
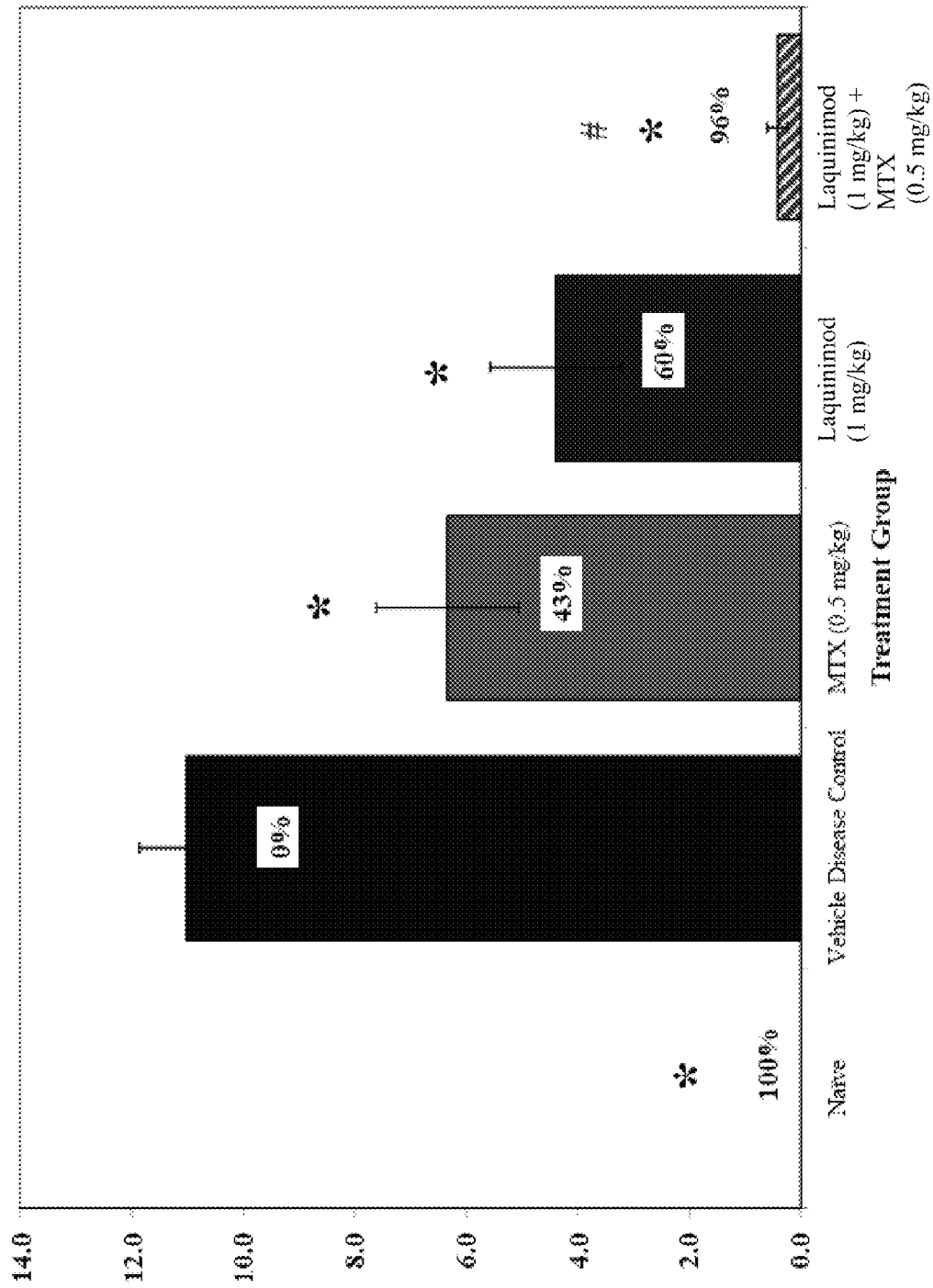

FIG. 2: FIG. 2 is a graph of Six Joint Animal Score: a bar graph showing the total score (sum of scores in individual histopathologic parameters) of the six joints) in the Control and Treatment Groups. ("LAQ" indicates Laquinimod, "MTX" indicates methotrexate) (*$p \leq 0.05$ student's t-test to vehicle, #$p \leq 0.05$ student's t-test to vehicle, n=10/treatment group, n=4/normal control.) The y-axis shows mean±SE Six Joint Animal Score (sum of individual parameters).

Figure 3:
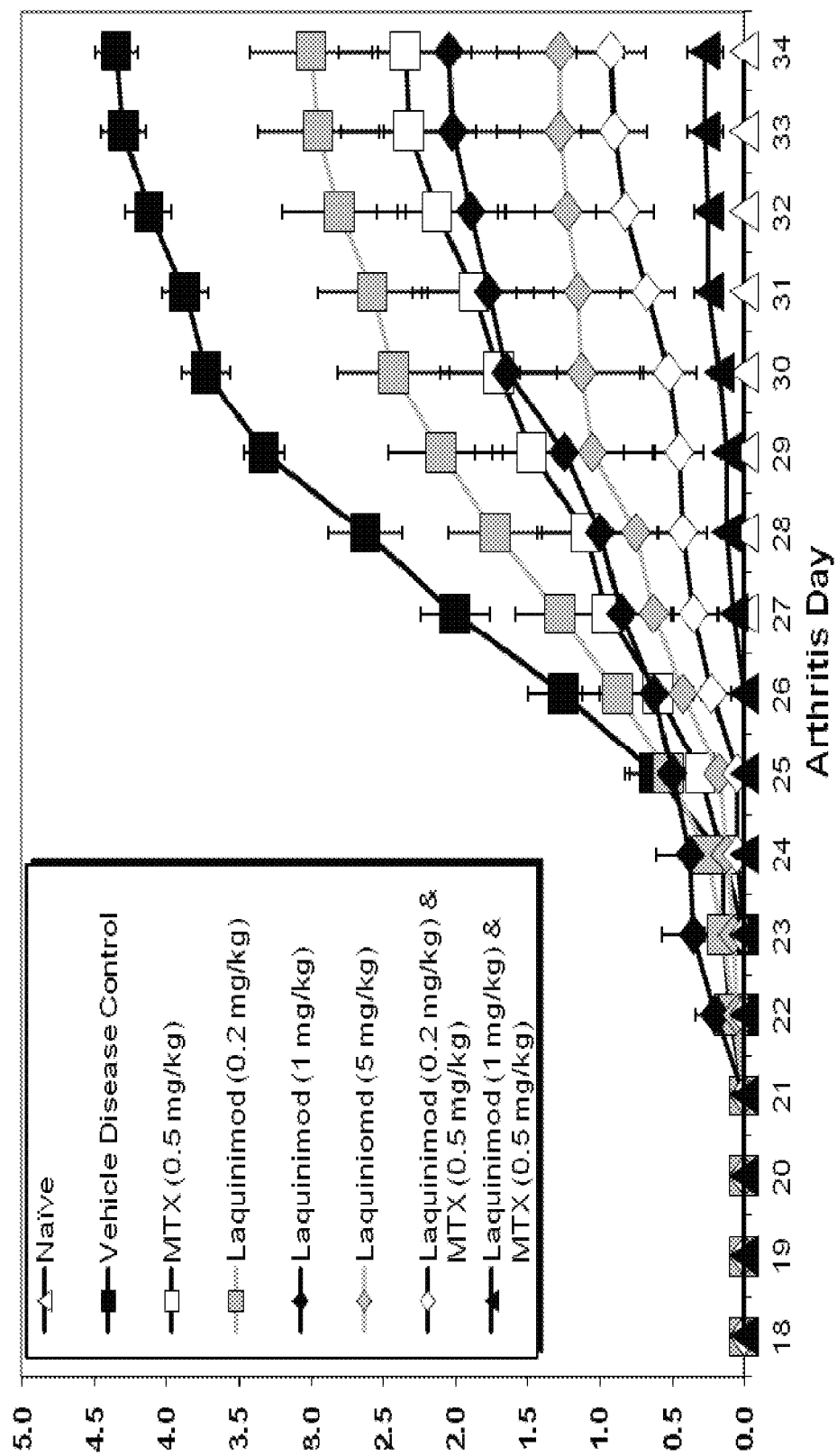

FIG. 3: FIG. 3 shows the clinical arthritis score progression in each treatment arm (Scores 0-5). (*$p \leq 0.05$ student's t-test to vehicle, #$p \leq 0.05$ student's t-test to MTX, n=10/treatment group, n=4/normal control.) The y-axis shows mean±SE Clinical Arthritis Score (scored 0-5).

DETAILED DESCRIPTION OF THE INVENTION

This invention provides a method of treating a subject afflicted with rheumatoid arthritis comprising periodically administering to the subject an amount of laquinimod or pharmaceutically acceptable salt thereof and an amount of methotrexate, wherein the amounts when taken together are effective to treat the subject.

In one embodiment, the amount of laquinimod or pharmaceutically acceptable salt thereof and the amount of methotrexate when taken together is more effective to treat the subject than when each agent is administered alone.

In one embodiment, the amount of laquinimod or pharmaceutically acceptable salt thereof and the amount of methotrexate when taken together is effective to reduce a clinical symptom of rheumatoid arthritis in the subject. In another embodiment, the pharmaceutically acceptable salt of laquinimod is laquinimod sodium.

In one embodiment, the periodic administration of laquinimod or pharmaceutically acceptable salt thereof is effected orally. In another embodiment, the amount of laquinimod administered is 0.0005-10 mg/kg/day. In yet another embodiment, the amount of laquinimod administered is 0.1-2.0 mg/day.

In one embodiment, the periodic administration of methotrexate is effected orally. In another embodiment, the amount of methotrexate administered is 0.02-1.0 mg/kg/day. In yet another embodiment, the amount of methotrexate administered is 1-3 mg/day.

In one embodiment, the method further comprises administration of nonsteroidal anti-inflammatory drugs (NSAIDs), salicylates, slow-acting drugs, gold compounds, hydroxychloroquine, sulfasalazine, combinations of slow-acting drugs, corticosteroids, cytotoxic drugs, immunosuppressive drugs and/or antibodies.

In one embodiment, the periodic administration of laquinimod or pharmaceutically acceptable salt thereof and methotrexate substantially eliminates a symptom associated with rheumatoid arthritis. In another embodiment, the periodic administration of laquinimod or pharmaceutically acceptable salt thereof and methotrexate reduces the severity of a symptom associated with rheumatoid arthritis. In yet another embodiment, the periodic administration of laquinimod or pharmaceutically acceptable salt thereof and methotrexate reduces the number of joints affected by a symptom associated with rheumatoid arthritis.

In one embodiment, the symptom is inflammation. In another embodiment, the symptom is formation of pannus tissue. In another embodiment, the symptom is cartilage damage. In another embodiment, the symptom is bone resorption.

In one embodiment, the periodic administration of laquinimod or pharmaceutically acceptable salt thereof and methotrexate reduces proteinuria in the subject. In another embodiment, the proteinuria reduction is measured by 24 hour urine protein, 24 hour protein to creatinine ratio, spot protein to creatinine ratio, 24 hour urine albumin, 24 hour albumin to creatinine ratio, spot albumin to creatinine ratio, or by a urinary dipstick. In yet another embodiment, the periodic administration of laquinimod or pharmaceutically acceptable salt thereof and methotrexate eliminates urinary sediments.

In one embodiment, each of the amount of laquinimod or pharmaceutically acceptable salt thereof when taken alone, and the amount of methotrexate when taken alone is effective to treat the subject. In another embodiment, either the amount of laquinimod or pharmaceutically acceptable salt thereof when taken alone, the amount of methotrexate when taken alone, or each such amount when taken alone is not effective to treat the subject.

In one embodiment, the subject is receiving methotrexate therapy prior to initiating laquinimod therapy. In another embodiment, the subject initiates periodic methotrexate administration prior to initiating periodic laquinimod administration.

In one embodiment, the administration of the laquinimod or pharmaceutically acceptable salt thereof substantially precedes the administration of methotrexate. In another embodiment, the administration of methotrexate substantially precedes the administration of laquinimod or pharmaceutically acceptable salt thereof.

In one embodiment, the subject is a mammal. In another embodiment, the mammal is human.

This invention provides a method of treating rheumatoid arthritis in a subject afflicted therewith comprising periodically administering to the subject an amount of laquinimod or pharmaceutically acceptable salt thereof and an amount of methotrexate, wherein the amounts when taken together are effective to treat the rheumatoid arthritis in the subject.

This invention also provides laquinimod or pharmaceutically acceptable salt thereof for use in combination with methotrexate in treating a subject afflicted with rheumatoid arthritis.

This invention also provides a pharmaceutical composition comprising an amount of laquinimod or pharmaceutically acceptable salt thereof and an amount of methotrexate for use in treating a subject afflicted with rheumatoid arthritis.

For the foregoing embodiments, each embodiment disclosed herein is contemplated as being applicable to each of the other disclosed embodiment.

It is understood that where a parameter range is provided, all integers within that range, and tenths thereof, are also provided by the invention. For example, "0.2-5 mg/kg/day" includes 0.2 mg/kg/day, 0.3 mg/kg/day, 0.4 mg/kg/day, 0.5 mg/kg/day, 0.6 mg/kg/day etc. up to 5.0 mg/kg/day.

Disclosed is a method of treating a subject afflicted with rheumatoid arthritis using laquinimod with methotrexate which provides a more efficacious treatment than each agent alone. In accordance with the subject invention, administration of laquinimod with methotrexate is particularly effective in combination to treat a subject afflicted with rheumatoid arthritis.

Terms

As used herein, and unless stated otherwise, each of the following terms shall have the definition set forth below.

As used herein, "laquinimod" means laquinimod acid or a pharmaceutically acceptable salt thereof.

As used herein, "a subject afflicted with rheumatoid arthritis" means a subject who was been affirmatively diagnosed to have rheumatoid arthritis.

As used herein, an "amount" or "dose" of laquinimod as measured in milligrams refers to the milligrams of laquinimod acid present in a preparation, regardless of the form of the preparation.

As used herein, "effective" when referring to an amount of laquinimod and/or methotrexate refers to the quantity of laquinimod and/or methotrexate that is sufficient to yield a desired therapeutic response without undue adverse side effects (such as toxicity, irritation, or allergic response) commensurate with a reasonable benefit/risk ratio when used in the manner of this invention.

As used herein, "substantially eliminates" a symptom associated with rheumatoid arthritis means decreasing the occurrence of that symptom by at least 96%.

As used herein, "treating" encompasses, e.g., inducing inhibition, regression, or stasis of a disorder, or lessening, suppressing, inhibiting, reducing the severity of, eliminating, or ameliorating a symptom of the disorder.

As used herein, "inhibition" of disease progression or disease complication in a subject means preventing or reducing the disease progression and/or disease complication in the subject.

As used herein, a "symptom" associated with rheumatoid arthritis includes any clinical or laboratory manifestation associated with rheumatoid arthritis and is not limited to what the subject can feel or observe. Inflammation is a symptom of rheumatoid arthritis.

As used herein, an "adverse event" or "AE" means any untoward medical occurrence in a clinical trial subject administered a medicinal product and which does not have a causal relationship with the treatment. An adverse event can therefore be any unfavorable and unintended sign including an abnormal laboratory finding, symptom, or diseases temporally associated with the use of an investigational medicinal product, whether or not considered related to the investigational medicinal product.

As used herein, "pharmaceutically acceptable carrier" refers to a carrier or excipient that is suitable for use with humans and/or animals without undue adverse side effects (such as toxicity, irritation, and allergic response) commensurate with a reasonable benefit/risk ratio. It can be a pharmaceutically acceptable solvent, suspending agent or vehicle, for delivering the instant compounds to the subject.

When referring to dosing, the designation "BID" indicates that the dose is administered twice daily. The designation "QD" indicates that the dose is administered once daily.

The use of laquinimod for rheumatoid arthritis had been previously suggested in, e.g., U.S. Pat. No. 6,077,851. However, the inventors have surprisingly found that the combination of laquinimod and methotrexate (MTX) is significantly more effective for the treatment of rheumatoid arthritis as compared to each agent alone.

A pharmaceutically acceptable salt of laquinimod as used in this application includes lithium, sodium, potassium, magnesium, calcium, manganese, copper, zinc, aluminum and iron. Salt formulations of laquinimod and the process for preparing the same are described, e.g., in U.S. Patent Application Publication No. 2005/0192315 and PCT International Application Publication No. WO 2005/074899, which are hereby incorporated by reference into this application.

A dosage unit may comprise a single compound or mixtures of compounds thereof. A dosage unit can be prepared for oral dosage forms, such as tablets, capsules, pills, powders, and granules.

Laquinimod can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit is preferably in a form suitable for oral administration. Laquinimod can be administered alone but is generally mixed with a pharmaceutically acceptable carrier, and co-administered in the form of a tablet or capsule, liposome, or as an agglomerated powder. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, dicalcium phosphate, calcium sulfate, mannitol, sorbitol, microcrystalline cellulose and the like. Suitable binders include starch, gelatin, natural sugars such as glucose or beta-lactose, corn starch, natural and synthetic gums such as acacia, tragacanth, or sodium alginate, povidone, carboxymethylcellulose, polyethylene glycol, waxes, and the like. Lubricants used in these dosage forms include sodium oleate, sodium stearate, sodium benzoate, sodium acetate, sodium chloride, stearic acid, sodium stearyl fumarate, talc and the like. Disintegrators include, without limitation, starch, methyl cellulose, agar, bentonite, xanthan gum, croscarmellose sodium, sodium starch glycolate and the like.

Specific examples of the techniques, pharmaceutically acceptable carriers and excipients that may be used to formulate oral dosage forms of the present invention are described, e.g., in U.S. Patent Application Publication No. 2005/0192315, PCT International Application Publication Nos. WO 2005/074899, WO 2007/047863, and WO 2007/146248.

General techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol.

40 (Gilbert S. Banker, Christopher T. Rhodes, Eds.). These references in their entireties are hereby incorporated by reference into this application.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

Assessment of the Effects of Anti-Inflammatory Agents Administered Orally (PO) and Daily (QD) in 35 Day DBA/10lahsd Mouse Semi-Established Type II Collagen Arthritis (MTTC/TV-9)

Introduction

Mice (DBA/11acJ, 1J or B10R111) reliably develop polyarthritis when immunized against bovine type II collagen (Trentham, 1977) using a variety of methodologies including day 0, day 15, 16 or 21 immunizations with and without concurrent boosting with endotoxin or recombinant IL-1 (Bendele, 2001). The disease that occurs is usually not symmetrical and any combination of paws/joints may be affected. Since caliper measurement of small mouse ankles is challenging, subjective clinical scoring systems are often used in conjunction with histological scoring methods. Treatments can be prophylactic (generally starting on days 16-21) or therapeutic (after observation of lesions) and depending on the immunization protocol used and extent of destruction desired, can extend from 10 days to several weeks. Lesions in affected joints resemble those occurring in rat collagen arthritis biologic agents such as Interleukin-1 receptor antagonist (IL-1ra) and the soluble TNF receptors (Wooley, 1993; Bakker, 1997; Joosten, 1994; Joosten, 1996; Geiger, 1993). Enhancement of disease incidence and severity has been demonstrated in mice immunized with type II collagen and concurrently given cytokines such as IL-1 (Hom, 1991; Hom, 1988).

This study is designed to determine the efficacy of potential anti-inflammatory agents (Laquinimod 0.2, 1, or 5 mg/kg) administered (po, qd) either alone or in combination with methotrexate (MTX) as potential anti-inflammatory agent in inhibiting the inflammation, cartilage destruction and bone resorption associated with semi-established type II collagen arthritis in mice. Mouse type II collagen arthritis is an art-recognized animal model for rheumatoid arthritis in humans (Bendele, 2001).

Here, male DBA/1OlaHsd mice with semi-established type II collagen arthritis were dosed orally (PO) daily (QD) on study days 18-33 with vehicle, Laquinimod (0.2, 1, or 5 mg/kg), methotrexate (0.5 mg/kg, MTX), or Laquinimod (0.2 or 1 mg/kg) in combination with MTX (0.5 mg/kg). Mice were terminated on day 34. Efficacy evaluable was based on animal body weights, daily clinical arthritis scores, arthritis scores expressed as area under the curve (AUC), and histopathology (groups 1-3, 5 and 8 only) on fore paws, hind paws, and knees from mice. Histopathology results were expressed as 4 paws, knees only, or 6 joint (knees included). Evaluation of serum anti-type II collagen antibody levels were also performed (groups 1-3, 6 and 8 only). All animals survived to study termination.

Animals

74 Male DBA/1OlaHsd (Harlan Inc.) that were 5-7 weeks old on arrival and weighed approximately 17-22 grams on study day 18 were obtained. Mice were at least 6 weeks at time of first immunization.

Materials: Agents or drugs in vehicle, Type II collagen (Elastin Products), Freund's complete adjuvant (with supplemental *M. tuberculosis,* 4 mg/ml) (Difco).

General Study Design

1. Animals (10/group for arthritis, 4/group for normal, housed 5/cage), were acclimated for 8 days after arrival that all animals are at least 7 weeks old.
2. Mice were anesthetized with Isoflurane and given 150 µl of Bovine Type II collagen in Freund's complete adjuvant injections (Sigma) containing bovine type II collagen (Elastin Products, Owensville, Mo.) (2 mg/ml) at the base of the tail (D0 and day 21).
3. Mice were randomized by body weight into treatment groups on study day 18.
4. MTX was provided by Bolder BioPATH, Inc. as a 1 mg/ml stock solution purchased from MWI and was prepared as a 0.05 mg/ml solution in 1% CMC for dosing at 10 ml/kg.
5. All dose solutions were prepared to deliver at 10 ml/kg (0.3 ml/30 g) mouse.
6. Treatment is initiated on study day 18 and continued once daily, every day (po, qd) according to Table 1.

TABLE 1

Treatment Dosing Schedule

| Group | N | Compound | Route | Regimen | Dose level (Mg/kg) | Dose Concentration (mg/ml) |
|---|---|---|---|---|---|---|
| 1 | 4 | Naïve | NA | NA | 0 | 0 |
| 2 | 10 | Vehicle Disease Control | NA | NA | 0 | 0 |
| 3 | 10 | MTX (0.5 mg/kg) | po | QD | 0.5 | 0.05 |
| 4 | 10 | Laquinimod | po | QD | 0.2 | 0.02 |
| 5 | 10 | Laquinimod | po | QD | 1 | 0.1 |
| 6 | 10 | Laquinimod | po | QD | 5 | 0.5 |
| 7 | 10 | Laquinimod and MTX (0.5 mg/kg) | po | QD | 0.2 | 0.02 |
| 8 | 10 | Laquinimod and MTX (0.5 mg/kg) | po | QD | 1 | 0.1 |

*For all test groups: n = 10, BW = 30 g, dose vol = 10 ml/kg, dose for 17 days

7. During the period of treatment, clinical scores were given for each of the paws (right front, left front, right rear, left rear) according to Table 2.

TABLE 2

Clinical Scoring Criteria for Fore and Hind Paws

| Score | Description |
|---|---|
| 0 | normal |
| 1 | 1 hind or fore paw joint affected or minimal diffuse erythema and swelling |
| 2 | 2 hind or fore paw joints affected or mild diffuse erythema and swelling |
| 3 | 3 hind or fore paw joints affected or moderate diffuse erythema and swelling |
| 4 | Marked diffuse erythema and swelling, or =4 digit joints affected |
| 5 | Severe diffuse erythema and severe swelling entire paw, unable to flex digits |

8. On days 21-35, onset of arthritis occurred. Mice were weighed on arthritis days 18, 20, 22, 24, 26, 28, 30, 32, and prior to tissue collection on day 34 (final day).

9. At necropsy, animals from all groups were bled via cardiac puncture for serum and terminated via cervical dislocation. Fore paws, hind paws and knees were removed and placed in 10% NBF. Whole blood was allowed to clot at room temperature for approximately 2 hours before being spun at 13,000 rpm for 8 minutes.
10. Processing of Joints: Following 1-2 days in fixative and then 4-5 days in decalcifier, the joints were processed, embedded, sectioned and stained with toluidine blue and H&E (2 slides per animal). Only fore and hind paws and knees were processed initially (6 joints/mouse).
11. Morphologic Pathology Methods: Histopathology was performed on groups 1-3, 5 and 8 only. After 1-2 days in fixative and 4-5 days in 5% formic acid for decalcification, tissues were trimmed, processed for paraffin embedding, sectioned at 8 µm and stained with toluidine blue (T blue). Hind paws, fore paws, and knees were embedded and sectioned in the frontal plane. Six joints from each animal were processed for histopathology elevation.
12. Tissue Processing and Evaluation:
   a. place joints in decalcifier,
   b. trim joints, wash, process tissues,
   c. embed joints,
   d. section tissues, stain tissues,
   e. histopathologic evaluation, and
   f. data processing, QC, prepare graphs and report.

Histopathologic Scoring Methods for Mouse Joints with Type II Collagen Arthritis When scoring paws or ankles from mice with lesions of type II collagen arthritis, severity of changes as well as number of individual joints affected must be considered. When only 1-3 joints of the paws or ankles out of a possibility of numerous metacarpal/metatarsal/digit or tarsal/tibiotarsal joints were affected, an arbitrary assignment of a maximum score of 1, 2 or 3 for parameters below (Tables 3-6) was given depending on severity of changes. If more than 3 joints were involved, the criteria below (Tables 3-6) were applied to the most severely affected/majority of joints.

TABLE 3

Inflammation

| Score | Description |
|---|---|
| 0 | normal |
| 1 | Minimal infiltration of inflammatory cells in synovium and periarticular tissue of affected joints |
| 2 | Mild infiltration of inflammatory cells. If referring to paws, generally restricted to affected joints (1-3 affected) |
| 3 | Moderate infiltration with moderate edema. If referring to paws, restricted to affected joints, generally 3-4 joints + wrist or ankle |
| 4 | Marked infiltration affecting most areas with marked edema, 1 or 2 unaffected joints may be present |
| 5 | Severe diffuse infiltration with severe edema affecting all joints and periarticular tissues |

TABLE 4

Pannus

| Score | Description |
|---|---|
| 0 | normal |
| 1 | Minimal infiltration of pannus in cartilage and subchondral bone, marginal zones |
| 2 | Mild infiltration with marginal zone destruction of hard tissue in affected joints |

TABLE 4-continued

Pannus

| Score | Description |
|---|---|
| 3 | Moderate infiltration with moderate hard tissue destruction in affected joints |
| 4 | Marked infiltration with marked destruction of joint architecture, affecting most joints |
| 5 | Severe infiltration associated with total or near total destruction of joint architecture, affects all joints |

TABLE 5

Cartilage Damage

| Score | Description |
|---|---|
| 0 | normal |
| 1 | Minimal: generally minimal to mild loss of toluidine blue staining with no obvious chondrocyte loss or collagen disruption in affected joints |
| 2 | Mild: generally mild loss of toluidine blue staining with focal areas of chondrocyte loss and/or collagen disruption in some affected joints |
| 3 | Moderate: generally moderate loss of toluidine blue staining with multifocal chondrocyte loss and/or collagen disruption in affected joints, some matrix remains on any affected surface with areas of severe matrix loss |
| 4 | Marked: marked loss of toluidine blue staining with multifocal marked (depth to deep zone) chondrocyte loss and/or collagen disruption in most joints, if knee-one surface with total to near total cartilage loss |
| 5 | Severe: severe diffuse loss of toluidine blue staining with multifocal severe (depth to tide mark) chondrocyte loss and/or collagen disruption in all joints, if knee-2 or more surfaces with total to near total cartilage loss |

TABLE 6

Bone Resorption

| Score | Description |
|---|---|
| 0 | normal |
| 1 | Minimal: small areas of resorption, not readily apparent on low magnification, rare osteoclasts in affected joints, restricted to marginal zones |
| 2 | Mild: more numerous areas of resorption, not readily apparent on low magnification, osteoclasts more numerous in affected joints, restricted to marginal zones |
| 3 | Moderate: obvious resorption of medullary trabecular and cortical bone without full thickness defects in cortex, loss of some medullary trabeculae, lesion apparent on low magnification, osteoclasts more numerous in affected joints |
| 4 | Marked: Full thickness defects in cortical bone, often with distortion of profile of remaining cortical surface, marked loss of medullary bone, numerous osteoclasts, affects most joints |
| 5 | Severe: Full thickness defects in cortical bone and destruction of joint architecture of all joints |

For each animal, the inflammation, pannus, cartilage damage and bone damage scores was determined for each of the 6 joints submitted. A sum total (all 6 joints) animal score and a six joint mean animal score was determined as well as sums and means for each of the individual parameters. Data were also expressed as means for paws (4 joints) or knees (2 joints). Parameters for the various groups are then compared to disease control animals.

Statistical Analysis

Clinical data for paw scores (means for animal) were analyzed by determining the area under the dosing curve (AUC) for study days 18-34. For calculation of AUC, the daily mean scores for each mouse were entered into Microsoft Excel and the area between the treatment days after the onset of disease to the final day was computed. Means for each group were determined and the percent inhibition from arthritis controls was calculated by comparing values for treated and normal animals. Statistical analysis of clinical and histopathology data was performed using a Student's t-test with significance set at $p \leq 0.05$.

Percent inhibition of clinical parameters and AUC is calculated using the following formula:

$$\% \text{ Inhibition} = B/A \times 100,$$

where A=Mean Disease Control−Mean Normal
B=Mean Treated−Mean Normal

Results

This study assesses the effects of anti-inflammatory agents administered po, qd in an animal model for human rheumatoid arthritis. The results indicate that the effect of the combination of laquinimod and methotrexate on rheumatoid arthritis symptoms is significantly more than the additive effect of each agent alone.

Body weight loss due to arthritis was significantly inhibited by treatment with 1 mg/kg Laquinimod+MTX (62% inhibition) as compared to vehicle treated disease controls. Body weight loss for this group was also significantly (69%) inhibited as compared MTX treated mice. Body weight loss for all other treatment groups did not differ significantly from vehicle controls.

Vehicle treated disease control mice had 100% disease incidence by study day 27. Mice treated with 0.2 mg/kg Laquinimod had 100% disease incidence by study day 28. Animals treated with MTX, 1 mg/kg Laquinimod, or 0.2 mg/kg Laquinimod+MTX had reduced disease incidence of 90% at study termination. Reduced disease incidence was also seen in mice treated with 5 mg/kg Laquinimod (70% incidence) or 1 mg/kg Laquinimod+MTX (60%).

Daily clinical arthritis scores were significantly reduced for mice treated with MTX (*significant days 27-34), 0.2 mg/kg Laquinimod (*d28-34), 1 mg/kg Laquinimod (*d25-34), 5 mg/kg Laquinimod (*d24-34), 0.2 mg/kg Laquinimod+MTX (*d24-34) or 1 mg/kg Laquinimod+MTX (*d24-34) as compared to vehicle controls. Daily clinical scores were also significantly reduced by treatment with 0.2 mg/kg Laquinimod+MTX (*d29-34) or 1 mg/kg Laquinimod+MTX (*d26-34) as compared to mice treated with MTX only. Prior to disease occurrence in the vehicle control group, daily clinical arthritis scores were significantly elevated in mice treated with 0.2 mg/kg Laquinimod (*d23), 1 mg/kg Laquinimod (*d22-24), or 5 mg/kg Laquinimod (*d22-23). (FIG. 3)

Clinical arthritis scores expressed as area under the curve (AUC) were significantly reduced for mice treated with MTX (50% reduction), 0.2 mg/kg Laquinimod (32%), 1 mg/kg Laquinimod (52%), 5 mg/kg Laquinimod (69%), 0.2 mg/kg Laquinimod+MTX (82%), or 1 mg/kg Laquinimod+MTX (95%) as compared to vehicle controls. Clinical arthritis scores AUC were also significantly reduced by treatment with 0.2 mg/kg Laquinimod+MTX (65%) or 1 mg/kg Laquinimod+MTX (90%) as compared to MTX treated mice.

Serum analysis for anti-TTC levels was performed on mice from groups 1-3, 6, and 8 only. Serum analysis revealed that vehicle control mice had anti-TTC levels of 27,062.50 units/ml. Serum Anti-TTC level were not significantly affected by treatment with 5 mg/kg Laquinimod, 1 mg/kg Laquinimod+MTX, or MTX as compared to vehicle controls.

Disease control animals had histopathology changes, consistent with those seen in type II collagen induced arthritis, in most joints, with scores ranging from minimal to severe. Microscopic alteration included infiltration of synovium and periarticular tissue with neutrophils and mononuclear inflammatory cells (inflammation), marginal zone pannus and bone resorption and cartilage damage (proteoglycan loss, chondrocyte death and collagen matrix destruction).

All paw histopathology parameters were significantly reduced toward normal for mice treated with 1 mg/kg Laquinimod (61% reduction of summed scores), 1 mg/kg Laquinimod+MTX (96%), or MTX (46%) as compared to vehicle controls. Treatment with 1 mg/kg Laquinimod+MTX also significantly (93%) reduced all paw histopathology parameters as compared to MTX treated mice.

All knee histopathology parameters were significantly reduced toward normal for mice treated with 1 mg/kg Laquinimod+MTX (97% reduction of summed scores) as compared to vehicle controls. Treatment of this group also significantly (95%) reduced all knee histopathology parameters as compared to MTX treated mice. Treatment with 1 mg/kg Laquinimod significantly reduced knee inflammation (51% reduction), pannus (59%), cartilage damage (62%), and summed knee scores (57%) as compared to vehicle controls.

All six-joint mean histopathology parameters were significantly reduced toward normal for mice treated with 1 mg/kg Laquinimod (60% reduction of summed scores), 1 mg/kg Laquinimod+MTX (96%), or MTX (43%) as compared to vehicle controls. Treatment with 1 mg/kg Laquinimod+MTX also significantly (93%) reduced all six-joint histopathology parameters as compared to MTX treated mice. (FIGS. 1 and 2)

Figure 1:
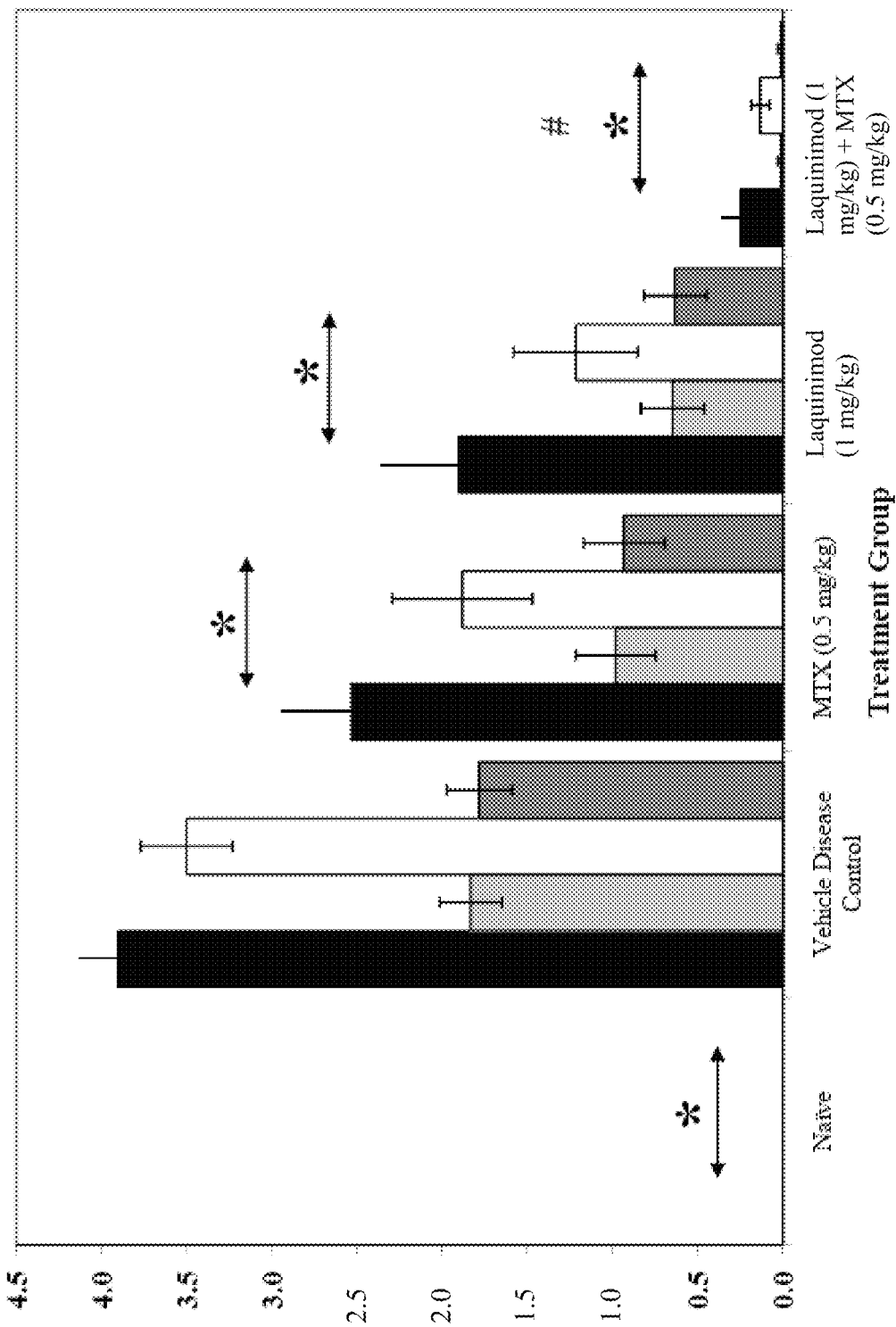
FIG. 1.

As shown in FIGS. 1 and 2, the administration of laquinimod in combination with methotrexate significantly reduced the severity of various symptoms associated with rheumatoid arthritis, including inflammation, pannus, cartilage damage and bone resorption on the six joints of the DBA/1OlaHsd mouse (four paws and two knees) as compared to the control group, the methotrexate only treatment group, and the laquinimod only treatment group.

FIG. 1 shows that the administration of laquinimod in combination with methotrexate substantially eliminated pannus and bone damage in the six joints of the test subjects, reducing their mean scores to nearly zero. FIG. 2 shows that the administration of laquinimod in combination with methotrexate substantially eliminated the overall symptoms associates with rheumatoid arthritis in the test subjects, reducing their cumulative score by 96%.

Thus, these results show that administration of laquinimod in combination with methotrexate is substantially more efficacious in treating a subject afflicted with active rheumatoid arthritis than each agent when administered alone. The inventors have surprisingly found that laquinimod and methotrexate work in synergy in the treatment of active rheumatoid arthritis.

REFERENCES

1. "Rheumatoid Arthritis" (1999) The Merck Manual, 7th Edition, pp 416-423.
2. 0130282 99506202. A double blind, randomized, repeat-dose, dose escalation study of ABR-215062 versus placebo in healthy volunteers and patients with multiple sclerosis. Active Biotech Research AB, Sweden. Final Clinical Trial Report, January 2002.
3. 03506207. An open safety study on laquinimod (ABR-215062) in patients with multiple sclerosis. Active Biotech Research AB, Sweden. Final Clinical Trial Report, April 2007.

4. 0430067 275-1061-01. Determination of the effects of ABR-212616, ABR-215050, ABR-215062 and ABR-215757 on the activities of CYP1A2 and CYP3A4 in cryopreserved human hepatocytes. In Vitro Technologies, USA. Final Report, February 2004.
5. 0430518 275-1081-02. Determination of the effects of ABR-215062 on CYP1A2 and CYP3A4 in cryopreserved human hepatocytes. In Vitro Technologies, USA. Final Report, August 2004.
6. 9830089. PNU-215045, PNU-215062: Effects on cytochrome P450 enzymes in female Sprague Dawley rats. Lund Research Center AB, Active Biotech Group, Sweden. Final Report, November 1998.
7. 9830133. PNU-215062: Effects on cytochrome P450 enzymes in female Sprague Dawley rats. Lund Research Center AB, Active Biotech Group, Sweden. Final Report, November 1998.
8. A two-period, open-label, one-sequence crossover study in healthy subjects to assess the potential interaction of fluconazole on laquinimod pharmacokinetics. PRACS Institute Cetero Research, ND, USA. Final Report, June 2009.
9. Arnett F, Edworthy S, Bloch D, McShane D, Fries J, Cooper N, Healey L, Kaplan S, Liang M, Luthra H (1988) "The American Rheumatism Association 1987 revised criteria for the classification of rheumatoid arthritis". *Arthritis Rheum.* 31 (3): 315-24.
10. Bakker, A C, Joosten L A B, Arntz O J, Helsen M A, Bendele A M, van de Loo A J, van den Berg W B. Gene therapy of murine collagen-induced arthritis: local expression of the human interleukin-1 receptor antagonist protein prevents onset. *Arthritis Rheum.* 1997; 40:893-900, 1997.
11. Bendele, A. M. (2001) "Animal Models of Rheumatoid Arthritis" *J Musculoskel Neuron Interact*, 1 (4):377-385.
12. Geiger T, Twobin H. Consenti-vargas A, Zingel O, Arnold J, Rordorf C, Glatt M, Vosbeck K. Neutralization of interleukin-1B activity in vivo with a monoclonal antibody alleviates collagen-induced arthritis in DBA/1 mice and prevents the associated acute phase response. *Clin Exp Rheumatol.* 1993; 11:515-522.
13. Hom J, Bendele A M, Carlsson D. In vivo administration with IL-1 accelerates the development of collagen-induced arthritis in mice. *J. Immunol.* 9188; 141:834-841.
14. Hom J, Gliszcznski V L, Cole H W, Bendele A M. Interleukin-1 mediated acceleration of type II collagen-induced arthritis: Effects of anti-inflammatory or anti-arthritic drugs. *Agents Actions.* 1991; 33:300-309.
15. Joosten L A B, Helsen M M A, van de Loo F A J and van den Berg W B. Amelioration of established type II collagen-induced arthritis (CIA) with anti-IL-1. *Agents Actions.* 1994; 41:C174-C176.
16. Joosten L A B, Helsen M M A, van de Loo F A J and van den Berg W B. Anticytokine treatment of established type II collagen-induced arthritis in DBA/1 mice. *Arthritis Rheum.* 1996; 39:797-809.
17. PCT International Application Publication No. WO 2007/047863, published Apr. 26, 2007, international filing date Oct. 18, 2006.
18. PCT International Application Publication No. WO 2007/146248, published Dec. 21, 2007, international filing date Jun. 12, 2007.
19. Polman, C. et al., (2005) "Treatment with laquinimod reduces development of active MRI lesions in relapsing MS", *Neurology.* 64:987-991.
20. Sandberg-Wollheim M, et al. (2005) "48-week open safety study with high-dose oral laquinimod in patients", *Mult Scler.* 11:S154 (Abstract).
21. TQT-LAQ-122. A Double-Blind, Randomized, Parallel Group, Thorough QT/QTc Trial in Healthy Men and Women to Assess the Effect of Laquinimod on Cardiac Repolarization Using a Clinical and a Supratherapeutic Dose Compared to Placebo, with Moxifloxacin as a Positive Control. PRACS Institute Cetero Research, ND, USA. Final Report, June 2009.
22. Trentham D E, Townes A S, Kang A H. Autoimmunity to type II collagen: an experimental model of arthritis. *J Exp Med.* 1977; 146 (3):857-868.
23. U.S. Pat. No. 6,077,851, issued Jun. 20, 2000 to Bjork, et al.
24. Wooley P H, Whalen J D, Chapman D L, Berger A E, Richard K A, Aspar D G and Staite N D. The effect of an interleukin-1 receptor antagonist protein on type II collagen-induced arthritis and antigen-induced arthritis in mice. *Arthritis Rheum.* 1993; 36:1305-1314.

What is claimed is:

1. A method of treating a subject afflicted with rheumatoid arthritis comprising administering to the subject daily, 0.2-2.0 mg of laquinimod or pharmaceutically acceptable salt thereof and 1-3 mg of methotrexate, wherein the amounts when taken together are more effective to treat the subject than when each agent is administered alone.

2. The method of claim 1, wherein the amount of laquinimod or pharmaceutically acceptable salt thereof and the amount of methotrexate when taken together is effective to reduce a clinical symptom of rheumatoid arthritis in the subject.

3. The method of claim 1, wherein the pharmaceutically acceptable salt of laquinimod is laquinimod sodium.

4. The method of claim 1, wherein the administration of laquinimod or pharmaceutically acceptable salt thereof is effected orally.

5. The method of claim 1, wherein the administration of methotrexate is effected orally.

6. The method of claim 1, further comprising administration of nonsteroidal anti-inflammatory drugs (NSAIDs), salicylates, hydroxychloroquine, sulfasalazine, corticosteroids, cytotoxic drugs, immunosuppressive drugs and/or antibodies.

7. The method of claim 1, wherein the administration of laquinimod or pharmaceutically acceptable salt thereof and methotrexate reduces the severity of a symptom associated with rheumatoid arthritis.

8. The method of claim 1, wherein the administration of laquinimod or pharmaceutically acceptable salt thereof and methotrexate reduces the number of joints affected by a symptom associated with rheumatoid arthritis.

9. The method of claim 1, wherein the subject is a mammal.

10. The method of claim 9, wherein the mammal is human.

* * * * *